United States Patent
Bardy et al.

(10) Patent No.: US 10,413,205 B2
(45) Date of Patent: *Sep. 17, 2019

(54) ELECTROCARDIOGRAPHY AND ACTIGRAPHY MONITORING SYSTEM

(71) Applicant: Bardy Diagnostics, Inc., Charlotte, NC (US)

(72) Inventors: Gust H. Bardy, Carnation, WA (US); Jason Felix, Vashon, WA (US); Jon MIkalson Bishay, Lexington, KY (US)

(73) Assignee: Bardy Diagnostics, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/681,064

(22) Filed: Aug. 18, 2017

(65) Prior Publication Data
US 2017/0367609 A1     Dec. 28, 2017

Related U.S. Application Data

(63) Continuation of application No. 14/082,108, filed on Nov. 16, 2013, now Pat. No. 9,737,224, which is a
(Continued)

(51) Int. Cl.
*A61B 5/0408* (2006.01)
*A61B 5/0205* (2006.01)
(Continued)

(52) U.S. Cl.
CPC ...... *A61B 5/04087* (2013.01); *A61B 5/02055* (2013.01); *A61B 5/04325* (2013.01);
(Continued)

(58) Field of Classification Search
CPC ............ A61B 5/04087; A61B 5/02055; A61B 5/04325; A61B 5/021; A61B 5/1118;
(Continued)

(56) References Cited

U.S. PATENT DOCUMENTS 3,215,136 A   11/1965   Holter et al.
3,569,852 A   3/1971    Berkovits
(Continued)

FOREIGN PATENT DOCUMENTS

DE   19955211   5/2001
EP   1859833    11/2007
(Continued)

OTHER PUBLICATIONS 15 of the Hottest Wearable Gadgets, URL http://thehottestgadgets.com/2008/09/the-15-hottest-wearable-gadgets-001253.
(Continued)

*Primary Examiner* — Mallika D Fairchild
*Assistant Examiner* — Minh Duc G Pham
(74) *Attorney, Agent, or Firm* — Patrick J. S. Inouye; Leonid Kisselev

(57) ABSTRACT

Physiological monitoring can be provided through an actigraphy sensor imbedded into an electrocardiography monitor, which correlates movement and electrocardiographic data. Physiological monitoring can be provided through a wearable monitor that includes two components, a flexible extended wear electrode patch and a removable reusable monitor recorder. The wearable monitor sits centrally on the patient's chest along the sternum. The patient can place an electrode patch anywhere within the general region of the sternum. The occurrence of actigraphy events are monitored by the monitor recorder through an actigraphy sensor. Actigraphy becomes a recordable actigraphy event occurrence when the movement of the wearable monitor and, therefore, the patient, exceeds a certain criteria threshold of acceleration or deceleration as detected by the actigraphy sensor. Certain actigraphy event occurrences as recorded by the monitor recorder are considered to be actionable, that is, of
(Continued)

sufficient importance to warrant flagging for further consideration to a following physician.

19 Claims, 9 Drawing Sheets

Related U.S. Application Data continuation-in-part of application No. 14/080,717, filed on Nov. 14, 2013, now Pat. No. 9,545,204, which is a continuation-in-part of application No. 14/080,725, filed on Nov. 14, 2013, now Pat. No. 9,730,593.

(60) Provisional application No. 61/882,403, filed on Sep. 25, 2013.

(51) Int. Cl.
    *A61B 5/0432* (2006.01)
    *A61B 5/11* (2006.01)
    A61B 5/021 (2006.01)
    A61B 5/03 (2006.01)
    A61B 5/04 (2006.01)
    A61B 5/0452 (2006.01)
    A61B 5/145 (2006.01)
    A61B 5/1455 (2006.01)

(52) U.S. Cl.
    CPC .............. *A61B 5/1118* (2013.01); *A61B 5/021* (2013.01); *A61B 5/03* (2013.01); *A61B 5/04017* (2013.01); *A61B 5/0452* (2013.01); *A61B 5/04085* (2013.01); *A61B 5/1117* (2013.01); *A61B 5/14532* (2013.01); *A61B 5/14551* (2013.01)

(58) Field of Classification Search
    CPC ............ A61B 5/04017; A61B 5/04085; A61B 5/1117; A61B 5/14532; A61B 5/14551
    USPC ....................................................... 600/301
    See application file for complete search history.

(56) References Cited

U.S. PATENT DOCUMENTS

| | | | |
|---|---|---|---|
| 3,699,948 A | 10/1972 | Ota et al. |
| 3,718,772 A | 2/1973 | Sanctuary |
| 3,893,453 A | 7/1975 | Goldberg |
| 4,123,785 A | 10/1978 | Cherry et al. |
| 4,151,513 A | 4/1979 | Menken et al. |
| 4,328,814 A | 5/1982 | Arkans |
| 4,441,500 A | 4/1984 | Sessions et al. |
| 4,532,934 A | 8/1985 | Kelen |
| 4,546,342 A | 10/1985 | Weaver et al. |
| 4,550,502 A | 11/1985 | Grayzel |
| 4,580,572 A | 4/1986 | Granek et al. |
| 4,635,646 A | 1/1987 | Gilles et al. |
| 4,653,022 A | 3/1987 | Koro |
| 4,716,903 A | 1/1988 | Hansen |
| 4,809,705 A | 3/1989 | Ascher |
| 4,915,656 A | 4/1990 | Alferness |
| 5,025,794 A | 6/1991 | Albert et al. |
| 5,107,480 A | 4/1992 | Naus |
| 5,168,876 A | 12/1992 | Quedens et al. |
| 5,215,098 A | 6/1993 | Steinhaus |
| 5,231,990 A | 8/1993 | Gauglitz |
| D341,423 S | 11/1993 | Bible |
| 5,263,481 A | 11/1993 | Axelgaard |
| 5,265,579 A | 11/1993 | Ferrari |
| 5,333,615 A | 8/1994 | Craelius et al. |
| 5,341,806 A | 8/1994 | Gadsby et al. |
| 5,348,008 A | 9/1994 | Bornn et al. |
| 5,355,891 A | 10/1994 | Wateridge et al. |
| 5,365,934 A | 11/1994 | Leon et al. |
| 5,365,935 A | 11/1994 | Righter et al. |
| 5,392,784 A | 2/1995 | Gudaitis |
| D357,069 S | 4/1995 | Plahn et al. |
| 5,402,780 A | 4/1995 | Faasse, Jr. |
| 5,402,884 A | 4/1995 | Gilman et al. |
| 5,450,845 A | 9/1995 | Axelgaard |
| 5,451,876 A | 9/1995 | Sendford et al. |
| 5,458,141 A | 10/1995 | Neil |
| 5,473,537 A | 12/1995 | Glazer et al. |
| 5,483,969 A | 1/1996 | Testerman et al. |
| 5,511,553 A | 4/1996 | Segalowitz |
| 5,540,733 A | 7/1996 | Testerman et al. |
| 5,546,952 A | 8/1996 | Erickson |
| 5,549,655 A | 8/1996 | Erickson |
| 5,579,919 A | 12/1996 | Gilman et al. |
| 5,582,181 A | 12/1996 | Ruess |
| D377,983 S | 2/1997 | Sabri et al. |
| 5,601,089 A | 2/1997 | Bledsoe et al. |
| 5,623,935 A | 4/1997 | Faisandier |
| 5,682,901 A | 11/1997 | Kamen |
| 5,697,955 A | 12/1997 | Stolte |
| 5,724,967 A | 3/1998 | Venkatachalam |
| 5,749,902 A | 5/1998 | Olsen et al. |
| 5,788,633 A | 8/1998 | Mahoney |
| 5,817,151 A | 10/1998 | Olsen et al. |
| 5,819,741 A | 10/1998 | Karlsson et al. |
| 5,850,920 A | 12/1998 | Gilman et al. |
| D407,159 S | 3/1999 | Roberg |
| 5,876,351 A | 3/1999 | Rohde |
| 5,906,583 A | 5/1999 | Rogel |
| 5,951,598 A | 9/1999 | Bishay et al. |
| 5,957,857 A | 9/1999 | Hartley |
| 5,984,102 A | 11/1999 | Tay |
| 6,032,064 A | 2/2000 | Devlin et al. |
| 6,038,469 A | 3/2000 | Karlsson et al. |
| 6,101,413 A | 8/2000 | Olsen et al. |
| 6,115,638 A | 9/2000 | Groenke |
| 6,117,077 A | 9/2000 | Del Mar et al. |
| 6,134,479 A | 10/2000 | Brewer et al. |
| 6,148,233 A | 11/2000 | Owen et al. |
| 6,149,602 A | 11/2000 | Arcelus |
| 6,149,781 A | 11/2000 | Forand |
| 6,188,407 B1 | 2/2001 | Smith et al. |
| D443,063 S | 5/2001 | Pisani et al. |
| 6,245,025 B1 | 6/2001 | Torok et al. |
| 6,246,330 B1 | 6/2001 | Nielsen |
| D445,507 S | 7/2001 | Pisani et al. |
| 6,269,267 B1 | 7/2001 | Bardy et al. |
| 6,272,385 B1 | 8/2001 | Bishay et al. |
| 6,298,255 B1 | 10/2001 | Cordero et al. |
| 6,301,502 B1 | 10/2001 | Owen et al. |
| 6,304,773 B1 | 10/2001 | Taylor et al. |
| 6,304,780 B1 | 10/2001 | Owen et al. |
| 6,304,783 B1 | 10/2001 | Lyster et al. |
| 6,374,138 B1 | 4/2002 | Owen et al. |
| 6,381,482 B1 | 4/2002 | Jayaraman et al. |
| 6,416,471 B1 | 7/2002 | Kumar et al. |
| 6,418,342 B1 | 7/2002 | Owen et al. |
| 6,424,860 B1 | 7/2002 | Karlsson et al. |
| 6,427,083 B1 | 7/2002 | Owen et al. |
| 6,427,085 B1 | 7/2002 | Boon et al. |
| 6,456,872 B1 | 7/2002 | Faisandier |
| 6,463,320 B1 | 10/2002 | Xue et al. |
| 6,546,285 B1 | 4/2003 | Owen et al. |
| 6,605,046 B1 | 8/2003 | Del Mar |
| 6,607,485 B2 | 8/2003 | Bardy |
| 6,611,705 B2 | 8/2003 | Hopman et al. |
| 6,671,545 B2 | 12/2003 | Fincke |
| 6,671,547 B2 | 12/2003 | Lyster et al. |
| 6,694,186 B2 | 2/2004 | Bardy |
| 6,704,595 B2 | 3/2004 | Bardy |
| 6,705,991 B2 | 3/2004 | Bardy |
| 6,719,701 B2 | 4/2004 | Lade |
| 6,754,523 B2 | 6/2004 | Toole |
| 6,782,293 B2 | 8/2004 | Dupelle et al. |
| 6,856,832 B1 | 2/2005 | Matsumura |
| 6,860,897 B2 | 3/2005 | Bardy |
| 6,866,629 B2 | 3/2005 | Bardy |

(56) References Cited

U.S. PATENT DOCUMENTS

| | | |
|---|---|---|
| 6,887,201 B2 | 5/2005 | Bardy |
| 6,893,397 B2 | 5/2005 | Bardy |
| 6,904,312 B2 | 6/2005 | Bardy |
| 6,908,431 B2 | 6/2005 | Bardy |
| 6,913,577 B2 | 7/2005 | Bardy |
| 6,944,498 B2 | 9/2005 | Owen et al. |
| 6,960,167 B2 | 11/2005 | Bardy |
| 6,970,731 B1 | 11/2005 | Jayaraman et al. |
| 6,978,169 B1 | 12/2005 | Guerra |
| 6,993,377 B2 | 1/2006 | Flick et al. |
| 7,020,508 B2 | 3/2006 | Stivoric et al. |
| 7,027,864 B2 | 4/2006 | Snyder et al. |
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| 7,294,108 B1 | 11/2007 | Bornzin et al. |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,108,035 B1 | 1/2012 | Bharmi |
| 8,116,841 B2 | 2/2012 | Bly et al. |
| 8,135,459 B2 | 3/2012 | Bardy et al. |
| 8,150,502 B2 | 4/2012 | Kumar et al. |
| 8,160,682 B2 | 4/2012 | Kumar et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,538,503 B2 | 9/2013 | Kumar et al. |
| 8,554,311 B2 | 10/2013 | Warner et al. |
| 8,560,046 B2 | 10/2013 | Kumar et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,628,020 B2 | 1/2014 | Beck |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,903,484 B2 | 12/2014 | Mazar |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,241,649 B2 | 1/2016 | Kumar et al. |
| 9,259,154 B2 | 2/2016 | Miller et al. |
| 9,277,864 B2 | 3/2016 | Yang et al. |
| 9,339,202 B2 | 5/2016 | Brockway et al. |
| 9,375,179 B2 | 6/2016 | Schultz et al. |
| 9,414,786 B1 | 8/2016 | Brockway et al. |
| 9,439,566 B2 | 9/2016 | Arne et al. |
| 9,603,542 B2 | 3/2017 | Veen et al. |
| 9,700,222 B2 | 7/2017 | Quinlan et al. |
| 9,770,182 B2 | 9/2017 | Bly et al. |
| 10,034,614 B2 | 7/2018 | Edic et al. |
| 10,045,708 B2 | 8/2018 | Dusan |
| 10,049,182 B2 | 8/2018 | Chefles et al. |
| 2002/0013538 A1 | 1/2002 | Teller |
| 2002/0013717 A1 | 1/2002 | Ando et al. |
| 2002/0016798 A1 | 2/2002 | Sakai |
| 2002/0103422 A1 | 8/2002 | Harder et al. |
| 2002/0120310 A1 | 8/2002 | Linden et al. |
| 2002/0128686 A1 | 9/2002 | Minogue et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0088019 A1 | 5/2004 | Rueter et al. |
| 2004/0093192 A1 | 5/2004 | Hasson et al. |
| 2004/0148194 A1 | 7/2004 | Wellons et al. |
| 2004/0163034 A1 | 8/2004 | Colbath et al. |
| 2004/0167416 A1 | 8/2004 | Lee |
| 2004/0207530 A1 | 10/2004 | Nielsen |
| 2004/0210165 A1 | 10/2004 | Marmaropoulos et al. |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0010139 A1 | 1/2005 | Aminian et al. |
| 2005/0096717 A1 | 5/2005 | Bishay et al. |
| 2005/0108055 A1 | 5/2005 | Ott et al. |
| 2005/0151640 A1 | 7/2005 | Hastings |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2005/0275416 A1 | 12/2005 | Hervieux et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0030904 A1 | 2/2006 | Quiles |
| 2006/0041201 A1 | 2/2006 | Behbehani et al. |

(56) References Cited

U.S. PATENT DOCUMENTS

| | | |
|---|---|---|
| 2006/0084883 A1 | 4/2006 | Linker |
| 2006/0111642 A1 | 5/2006 | Baura et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0229522 A1 | 10/2006 | Barr |
| 2006/0235320 A1 | 10/2006 | Tan et al. |
| 2006/0253006 A1 | 11/2006 | Bardy |
| 2006/0264730 A1 | 11/2006 | Stivoric et al. |
| 2006/0264767 A1 | 11/2006 | Shennib |
| 2007/0003115 A1 | 1/2007 | Patton et al. |
| 2007/0038057 A1 | 2/2007 | Nam et al. |
| 2007/0050209 A1 | 3/2007 | Yered |
| 2007/0078324 A1 | 4/2007 | Wijisiriwardana |
| 2007/0088406 A1 | 4/2007 | Bennett et al. |
| 2007/0089800 A1 | 4/2007 | Sharma |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0131595 A1 | 6/2007 | Jansson et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0051668 A1 | 2/2008 | Bardy |
| 2008/0058661 A1 | 3/2008 | Bardy |
| 2008/0088467 A1 | 4/2008 | Al-Ali et al. |
| 2008/0091089 A1 | 4/2008 | Guillory et al. |
| 2008/0091097 A1 | 4/2008 | Linti et al. |
| 2008/0108890 A1 | 5/2008 | Teng et al. |
| 2008/0114232 A1 | 5/2008 | Gazit |
| 2008/0139953 A1 | 6/2008 | Baker et al. |
| 2008/0143080 A1 | 6/2008 | Burr |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0294024 A1 | 11/2008 | Cosentino et al. |
| 2008/0306359 A1 | 12/2008 | Zdeblick et al. |
| 2008/0312522 A1 | 12/2008 | Rowlandson |
| 2009/0012412 A1 | 1/2009 | Wesel |
| 2009/0012979 A1 | 1/2009 | Bateni et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0156908 A1* | 6/2009 | Belalcazar ........... A61B 5/0031 600/301 |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0174229 A1 | 7/2010 | Hsu et al. |
| 2010/0177100 A1 | 7/2010 | Carnes et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0223020 A1 | 9/2010 | Goetz |
| 2010/0234715 A1 | 9/2010 | Shin et al. |
| 2010/0234716 A1 | 9/2010 | Engel |
| 2010/0280366 A1 | 11/2010 | Arne et al. |
| 2010/0312188 A1 | 12/2010 | Robertson et al. |
| 2010/0324384 A1 | 12/2010 | Moon et al. |
| 2011/0021937 A1 | 1/2011 | Hugh et al. |
| 2011/0054286 A1 | 3/2011 | Crosby et al. |
| 2011/0060215 A1 | 3/2011 | Tupin et al. |
| 2011/0066041 A1 | 3/2011 | Pandia et al. |
| 2011/0077497 A1 | 3/2011 | Oster et al. |
| 2011/0105861 A1 | 5/2011 | Derchak et al. |
| 2011/0144470 A1 | 6/2011 | Mazar et al. |
| 2011/0160548 A1 | 6/2011 | Forster |
| 2011/0224564 A1 | 9/2011 | Moon et al. |
| 2011/0237922 A1 | 9/2011 | Parker, III et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2011/0288605 A1* | 11/2011 | Kaib .................... A61B 5/0006 607/5 |
| 2012/0003933 A1 | 1/2012 | Baker et al. |
| 2012/0029306 A1 | 2/2012 | Paquet et al. |
| 2012/0029315 A1 | 2/2012 | Raptis et al. |
| 2012/0029316 A1 | 2/2012 | Raptis et al. |
| 2012/0035432 A1 | 2/2012 | Katra et al. |
| 2012/0078127 A1 | 3/2012 | McDonald et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0165645 A1 | 6/2012 | Russel et al. |
| 2012/0306662 A1 | 6/2012 | Vosch et al. |
| 2012/0172695 A1 | 7/2012 | Ko et al. |
| 2012/0238910 A1 | 9/2012 | Nordstrom |
| 2012/0253847 A1 | 10/2012 | Dell'Anno et al. |
| 2012/0302906 A1 | 11/2012 | Felix et al. |
| 2012/0330126 A1 | 12/2012 | Hoppe et al. |
| 2013/0041272 A1 | 2/2013 | Javier et al. |
| 2013/0077263 A1 | 3/2013 | Oleson et al. |
| 2013/0079611 A1 | 3/2013 | Besko |
| 2013/0085347 A1* | 4/2013 | Manicka ............ A61B 5/0205 600/301 |
| 2013/0085403 A1 | 4/2013 | Gunderson et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0225963 A1 | 8/2013 | Kodandaramaiah et al. |
| 2013/0225966 A1 | 8/2013 | Macia Barber et al. |
| 2013/0231947 A1* | 9/2013 | Shusterman ........ G06F 19/3418 705/2 |
| 2013/0243105 A1 | 9/2013 | Lei et al. |
| 2013/0274584 A1 | 10/2013 | Finlay et al. |
| 2013/0275158 A1 | 10/2013 | Fahey |

(56) References Cited

U.S. PATENT DOCUMENTS

| | | |
|---|---|---|
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325081 A1 | 12/2013 | Karst et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0056452 A1 | 2/2014 | Moss et al. |
| 2014/0088399 A1 | 3/2014 | Lian et al. |
| 2014/0140359 A1 | 5/2014 | Kalevo et al. |
| 2014/0180027 A1 | 6/2014 | Buller |
| 2014/0189928 A1 | 7/2014 | Oleson et al. |
| 2014/0206977 A1 | 7/2014 | Bahney et al. |
| 2014/0214134 A1 | 7/2014 | Peterson |
| 2014/0215246 A1* | 7/2014 | Lee ................... G06F 1/3206 713/323 |
| 2014/0249852 A1 | 9/2014 | Proud |
| 2014/0296651 A1 | 10/2014 | Stone |
| 2014/0343390 A1 | 11/2014 | Berzowska et al. |
| 2014/0358193 A1 | 12/2014 | Lyons et al. |
| 2014/0364756 A1 | 12/2014 | Brockway et al. |
| 2015/0048836 A1 | 2/2015 | Guthrie et al. |
| 2015/0065842 A1 | 3/2015 | Lee et al. |
| 2015/0177175 A1 | 6/2015 | Elder et al. |
| 2015/0250422 A1 | 9/2015 | Bay |
| 2015/0257670 A1 | 9/2015 | Ortega et al. |
| 2015/0305676 A1 | 11/2015 | Shoshani |
| 2015/0359489 A1 | 12/2015 | Baudenbacher et al. |
| 2016/0135746 A1 | 5/2016 | Kumar et al. |
| 2016/0217691 A1 | 7/2016 | Kadobayashi et al. |
| 2019/0021671 A1 | 1/2019 | Kumar et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | H11188015 | 7/1999 |
| JP | 2004129788 | 4/2004 |
| JP | 2007082938 | 4/2007 |
| JP | 2009219554 | 10/2009 |
| WO | 199852463 | 11/1998 |
| WO | 00/78213 | 12/2000 |
| WO | 2003032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2008092098 | 7/2008 |
| WO | 2009036306 | 3/2009 |
| WO | 2009036313 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |

OTHER PUBLICATIONS

Alivecor, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al. "Monitoring Body Temperature of Newborn Infants at Neonatal Intensive Care Units Using Wearable Sensors," BodyNets 2010, Corfu Island, Greece. Sep. 10-12, 1210.

Epstein, Andrew E. et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit Tracker, URL <http://www.fitbit.com/> (Web page cached on Sep. 10, 2008.).

Smith, Jawbone Up, URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid," Technology Review, MIT. (May 1, 2009).

Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013.).

Nike+ Fuel Band, URL <http://www.nike.com/us/en_us/c/nikeplus-fuelband> (Web page cached on Jan. 11, 2013.).

P. Libby et al.,"Braunwald's Heart Disease—A Textbook of Cardiovascular Medicine," Chs. 11, pp. 125-148 and 12, pp. 149-193 (8th ed. 2008), American Heart Association.

Polar Loop, URL <http://www.dcrainmaker.com/2013/09/polar-loop-firstlook.html>.

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Sleepview, URL <http://www.clevemed.com/sleepview/overview.shtml> (Web page cached on Sep. 4, 2013.).

Actigraphy/ Circadian Rhythm SOMNOwatch, URL <http://www.somnomedics.eu/news-events/publications/somnowatchtm.html> (Web page cached on Jan. 23, 2010).

Zio Event Card, URL <http://www.irhythmtech.com/zio-solution/zio-event/> (Web page cached on Mar. 11, 2013.).

Zio Patch System, URL <http://www.irhythmtech.com/zio-solution/zio-system/index.html> (Web page cached on Sep. 8, 2013).

Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.

Anonymous. "Omegawave Launches Consumer App 2.0 in U.S. Endurance Sportswire—Endurance Sportswire." Jul. 11, 2011 URL:http://endurancesportswire.com/omegawave-launches-consumer-app-2-0-in-u-s/.

Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.

Daoud et al. "Fall Detection Using Shimmer Technology and Multiresolution Analysis." Aug. 2, 2013. URL: https://decibel.ni.com/content/docs/DOC-26652.

Libbus. "Adherent Cardiac Monitor With Wireless Fall Detection for Patients With Unexplained Syncope." Abstracts of the First AMA-IEEE Medical Technology Conference on Individualized Healthcare. May 22, 2010.

Duttweiler et al., "Probability Estimation in Arithmetic and Adaptive-Huffman Entropy Coders," IEEE Transactions on Image Processing. vol. 4, No. 3, Mar. 1, 1995, pp. 237-246.

Gupta et al., "An ECG Compression Technique for Telecardiology Application," India Conference (INDICON), 2011 Annual IEEE, Dec. 16, 2011, pp. 1-4.

Nave et al., "ECG Compression Using Long-Term Prediction," IEEE Transactions on Biomedical Engineering, IEEE Service Center, NY, USA, vol. 40, No. 9, Sep. 1, 1993, pp. 877-885.

(56) References Cited

OTHER PUBLICATIONS

Skretting et al., "Improved Huffman Coding Using Recursive Splitting," NORSIG, Jan. 1, 1999.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i_1399-5618.2006.00364.x.
Varicrad-Kardi Software User's Manual Rev. 1.1, Jul. 8, 2009 (Jul. 8, 2009), XP002757888, retrieved from the Internet: URL:http://www.ehrlich.tv/KARDiVAR-Software.pdf [retrieved on May 20, 2016].
https://web.archive.org/web/20130831204020/http://www.biopac.com/research.asp?CatID=37&Main=Software (Aug. 2013).
Adinstruments:ECG Analysis Module for LabChart & PowerLab, 2008.
BIOPAC Systems, Inc. #A5148-Automated ECG Analysis , Mar. 24, 2006.
G. G. Ivanov, "HRV Analysis Under the Usage of Different Electrocardiopraphy Systems," Apr. 15, 2008 (Apr. 15, 2008), XP55511209, Retrieved from the Internet: URL:http://www.drkucera.eu/upload_doc/hrv_analysis_(methodical_recommendations).pdf [retrieved on Oct. 1, 2018].

\* cited by examiner

160

ELECTROCARDIOGRAPHY AND ACTIGRAPHY MONITORING SYSTEM

CROSS-REFERENCE TO RELATED APPLICATION

This non-provisional patent application is a continuation of U.S. Pat. No. 9,737,224, issued Aug. 22, 2017, which is a continuation-in-part of U.S. Pat. No. 9,545,204, issued Jan. 17, 2017, and a continuation-in-part of U.S. Pat. No. 9,730, 593, issued Aug. 15, 2017; and further claims priority under 35 U.S.C. § 119(e) to U.S. Provisional Patent application, Ser. No. 61/882,403, filed Sep. 25, 2013, the disclosures of which are incorporated by reference

FIELD

This application relates in general to electrocardiographic monitoring and, in particular, to electrocardiography and actigraphy monitoring system.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

Diagnostic efficacy can be improved, when appropriate, through the use of long-term extended ECG monitoring. Recording sufficient ECG and related physiology over an extended period is challenging, and often essential to enabling a physician to identify events of potential concern. A 30-day observation period is considered the "gold standard" of ECG monitoring, yet achieving a 30-day observation period has proven unworkable because such ECG monitoring systems are arduous to employ, cumbersome to the patient, and excessively costly. Ambulatory monitoring in-clinic is implausible and impracticable. Nevertheless, if a patient's ECG could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of ECG electrodes is complicated by skin irritation and the inability ECG electrodes to maintain continual skin contact after a day or two. Moreover, time, dirt, moisture, and other environmental contaminants, as well as per ration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Notwithstanding the cause of electrode dislodgment, depending upon the type of ECG monitor employed, precise re-placement of a dislodged ECG electrode maybe essential to ensuring signal capture at the same fidelity. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, Holter monitors are widely used for long-term extended ECG monitoring. Typically, they are used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter monitor (or event) can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic. The relationship of cardiac events to activity is crucial to proper diagnosis and patient management and the correlation of cardiac events to activity is a valuable patient care tool.

The ZIO XT Patch and ZIO Event Card devices, manufactured by iRhythm Tech., Inc., San Francisco, Calif., are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components, including battery, and physical electrodes into a unitary assembly that adheres to the patient's skin. The ZIO XT Patch device uses adhesive sufficiently strong to support the weight of both the monitor and the electrodes over an extended period of time and to resist disadherance from the patient's body, albeit at the cost of disallowing removal or relocation during the monitoring period. Moreover, throughout monitoring, the battery is continually depleted and battery capacity can potentially limit overall monitoring duration. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of atrial (P-wave) signals.

The diagnosis, prognosis, and treatment of medical conditions can be further improved by concomitant recording of ECG and human activity. For instance, the correlation of motor activity and cardiovascular stress is important for optimizing and monitoring exercise and rehabilitation progress. Certain movement, such as a fall, may precipitate an episode of heart disease; conversely, heart conditions may restrict a person's movement or alter movement patterns.

An actigraphy sensor, such as an accelerometer, has conventionally been used as a non-invasive method to monitor sleep, activity and movement. Sleep actigraphs are generally watch-shaped and worn on the wrist of the non-dominant arm, and can be worn for weeks. Activity actigraphs are worn and used similar to a pedometer: around waist, near the hip. They are useful for determining the amount of activity and possibly calories. They can be worn for a number of days. Movement actigraphs are generally larger and worn on the shoulder of the dominant arm. They contain 3-D actigraph as opposed to a single dimension one used in sleep actigraph and activity actigraph, and tend to have a high sample rate and a large memory, as a result they are often used for only a few hours.

The correlation of ECG and movement is beneficial to patient care, and the benefit increases with long-term monitoring. Wearing two separate devices, one for ECG monitoring and another for actigraphy, however, creates its own problems. For example, recordings from two separate devices are generally not synchronized. Also, a patient may misplace the actigraphy sensor, resulting in misinterpretation of movements. For instance, the SOMNOwatch actigraphy monitor, manufactured by SOMNOmedics, Randersacker, Germany, is a wearable watch-shaped monitoring device that records sleep actigraphy and recognizes sleep/wake rhythm, in addition to reading an ECG and recording heart rate. However, the SOMNOwatch actigraphy monitor can only store the raw data of a single channel ECG for up to 18 hours, requires a software system to synchronize heart rate with motor activity, and does not record specific movement.

Therefore, a need remains for an extended wear continuously recording ECG monitor coupled with an actigraphy sensor practicably capable of being worn for a long period of time and correlating cardiovascular events with movements, in both men and women, and capable of recording atrial signals reliably.

A further need remains for a device capable of recording signals ideal for arrhythmia discrimination, especially a device designed for atrial activity recording in combination with actigraphy sensing.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum, the area most likely to record high quality atrial signals or P-waves. In addition, the occurrence of actigraphy events are monitored by the monitor recorder through an actigraphy sensor. Actigraphy becomes a recordable actigraphy event occurrence when the movement of the wearable monitor and, therefore, the patient, exceeds a certain criteria threshold of acceleration or deceleration as detected by the actigraphy sensor. Certain actigraphy event occurrences as recorded by the monitor recorder are considered to be actionable, that is, of sufficient importance to warrant flagging for further consideration to a following physician. For instance, the occurrence of a fall event could signal the onset of myocardial infarction in the patient, or, under different circumstances, could be found to have been precipitated by myocardial infarctional onset. The occurrence of an actigraphy event is identified as actionable based on a filtering criteria.

In one embodiment, an electrocardiography and actigraphy monitoring system is provided. The system includes a monitor recorder that includes a sealed housing adapted to be removably secured into a non-conductive receptacle on a disposable extended wear electrode patch and electronic circuitry within the sealed housing. The electronic circuitry includes an externally-powered flash memory electrically interfaced with an externally-powered micro-controller and operable to store physiological data from at least two physiological data channels into a single data record; an electrocardiographic front end circuit electrically interfaced to the externally-powered micro-controller and operable to sense electrocardiographic signals through electrocardiographic electrodes provided on the disposable extended wear electrode patch; an actigraphy sensor electrically interfaced with the micro-controller and operable to sense one or more actigraphy event occurrences based on movement of the sensor using an actigraphy event occurrence criteria and to send an interrupt request (IRQ) signal to the micro-controller upon sensing each of the actigraphy event occurrences; and an externally-powered micro-controller operable to execute under micro-programmable control, the micro-controller further operable to sample the electrocardiographic signals and to sample one of the actigraphy event occurrences sensed by the actigraphy sensor upon receiving one of the IRQ signals, to embed samples of the electrocardiographic signals within one of the physiological data channels for storage into the data record in the memory and to embed the samples of the actigraphy event occurrences into another one of the physiological data channels for storage into the data record in the memory.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, would cause chafing, irritation, frustration, and annoyance, leading to low patient compliance.

The foregoing aspects enhance ECG monitoring performance and quality, facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis.

Finally, the foregoing aspects as relevant to monitoring are equally applicable to recording other physiological measures, such as temperature, respiratory rate, blood sugar, oxygen saturation, and blood pressure, as well as other measures of body chemistry and physiology.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
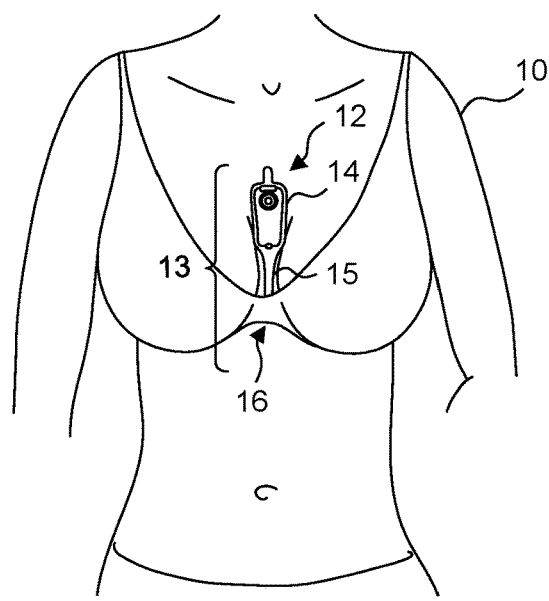
FIGS. 1 and 2 are diagrams showing, by way of examples, an extended wear electrocardiography and actigraphy monitor, including a monitor recorder in accordance with one embodiment, respectively fitted to the sternal region of a female patient and a male patient.
Figure 2:
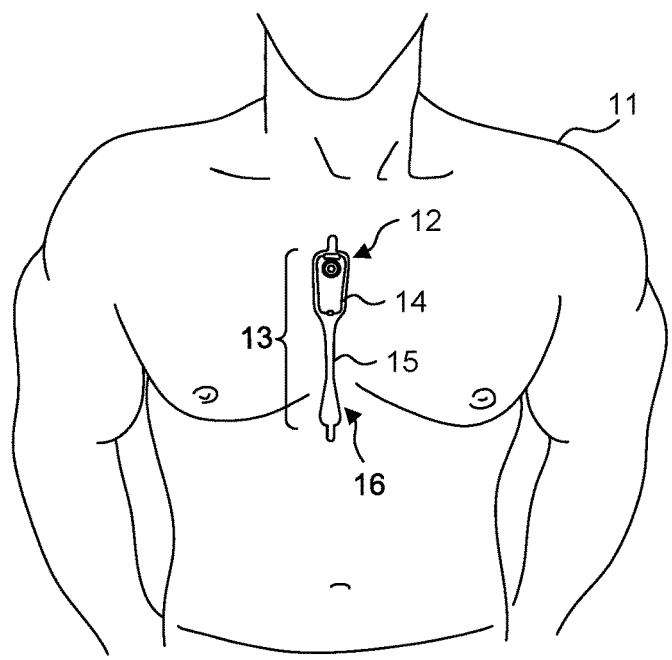

Physiological monitoring can be provided through a wearable monitor that includes two components, a flexible extended wear electrode patch and a removable reusable monitor recorder. FIGS. 1 and 2 are diagrams showing, by way of examples, an extended wear electrocardiography and physiological sensor monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity while simultaneously facilitating comfortable long-term wear for many weeks. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the Xiphoid process facilitates sensing of ventricular activity and provides superior recordation of the QRS interval.

Figure 3:
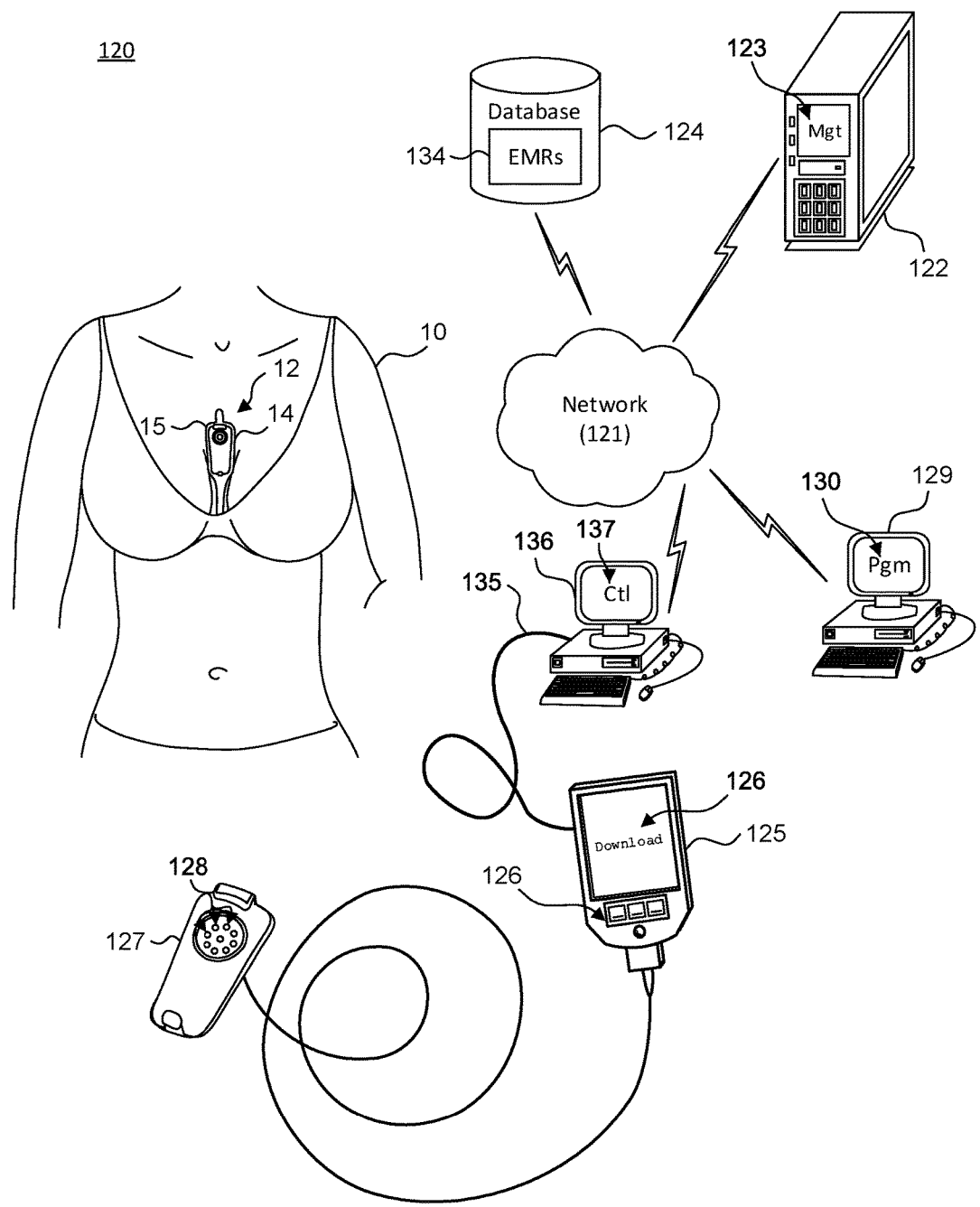
FIG. 3 is a functional block diagram showing a system for remote interfacing of a combined ECG and actigraphy monitor recorder in accordance with one embodiment inserted.

When operated standalone, the monitor recorder 14 of the extended wear electrocardiography and physiological sensor monitor 12 senses and records the patient's ECG data into an onboard memory. FIG. 3 is a functional block diagram showing a system 120 for remote interfacing of an extended wear electrocardiography and actigraphy sensor monitor 12 in accordance with one embodiment. The monitor recorder 14 is a reusable component that can be fitted during patient monitoring into a non-conductive receptacle provided on the electrode patch 15, as further described infra with reference to FIG. 4, and later removed for offloading of stored ECG data or to receive revised programming. The monitor recorder 14 can then be connected to a download station 125, which could be a programmer or other device that permits the retrieval of stored ECG monitoring data, execution of diagnostics on or programming of the monitor recorder 14, or performance of other functions. The monitor recorder 14 has a set of electrical contacts (not shown) that enable the monitor recorder 14 to physically interface to a set of terminals 128 on a paired receptacle 127 of the download station 125. In turn, the download station 125 executes a communications or offload program 126 ("Offload") or similar program that interacts with the monitor recorder 14 via the physical interface to retrieve the stored ECG monitoring data or to execute diagnostics on or reprogram the monitor recorder's program memory unit and thereby revise the subsequent operation of the monitor recorder 14. The download station 125 could be a server, personal computer, tablet or handheld computer, smart mobile device, or purpose-built programmer designed specific to the task of interfacing with a monitor recorder 14. Still other forms of download station 125 are possible. In addition, the wearable monitor 12 can interoperate with other devices, as further described in detail in commonly-assigned U.S. Pat. No. 9,433,367, issued Sep. 6, 2016, the disclosure of which is incorporated by reference.

Figure 13:
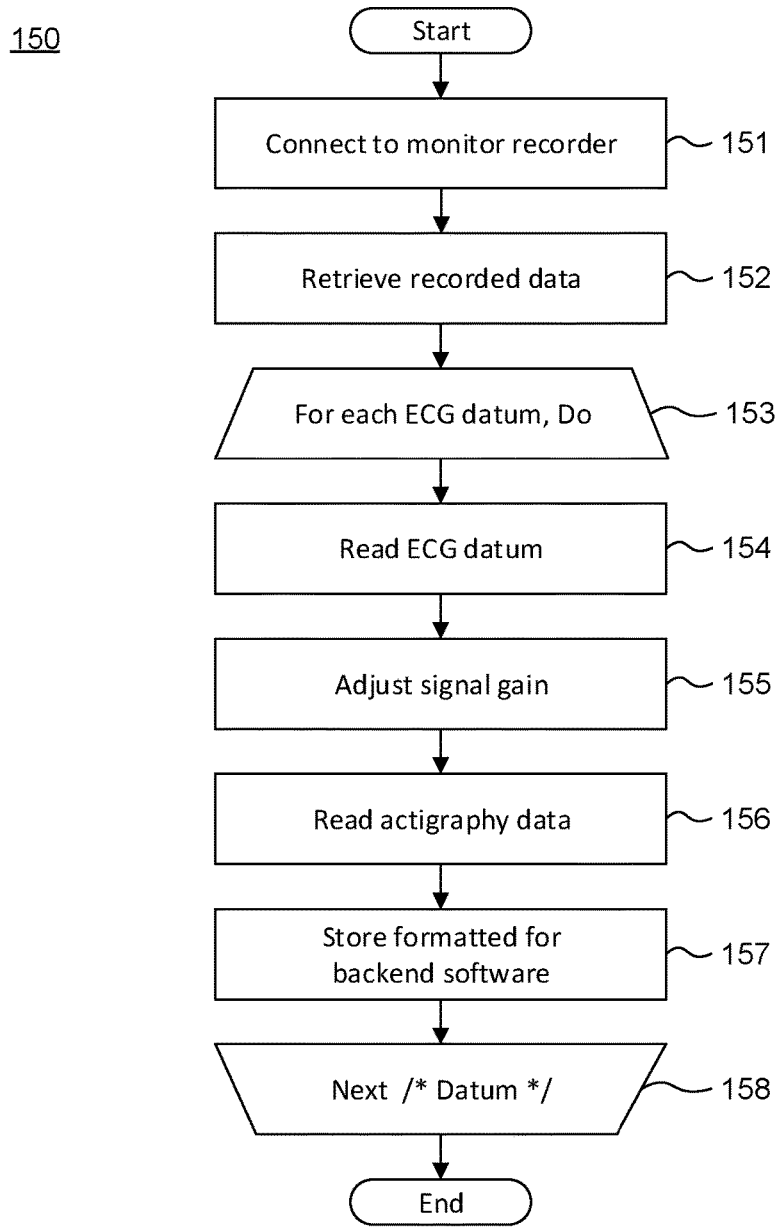
FIG. 13 is a flow diagram showing a method for offloading and converting ECG and other physiological data from of an extended wear electrocardiography and actigraphy monitor in accordance with one embodiment.

Upon retrieving stored ECG monitoring data from a monitor recorder 14, middleware first operates on the retrieved data to adjust the ECG capture quality, as necessary, and to convert the retrieved data into a format suitable for use by third party post-monitoring analysis software, as further described infra with reference to FIG. 13. The formatted data can then be retrieved from the download station 125 over a hard link 135 using a control program 137 ("Ctl") or analogous application executing on a personal computer 136 or other connectable computing device, via a communications link (not shown), whether wired or wireless, or by physical transfer of storage media (not shown). The personal computer 136 or other connectable device may also execute middleware that converts ECG data and other information into a format suitable for use by a third-party post-monitoring analysis program, as further described infra with reference to FIG. 13. Note that formatted data stored on the personal computer 136 would have to be maintained and safeguarded in the same manner as electronic medical records (EMRs) 134 in the secure database 124, as further discussed infra. In a further embodiment, the download station 125 is able to directly interface with other devices over a computer communications network 121, which could be some combination of a local area network and a wide area network, including the Internet, over a wired or wireless connection.

A client-server model could be used to employ a server 122 to remotely interface with the download station 125 over the network 121 and retrieve the formatted data or other information. The server 122 executes a patient management program 123 ("Mgt") or similar application that stores the retrieved formatted data and other information in a secure database 124 cataloged in that patient's EMRs 134. In addition, the patient management program 123 could manage a subscription service that authorizes a monitor recorder 14 to operate for a set period of time or under pre-defined operational parameters, such as described in commonly-assigned U.S. Pat. No. 9,655,538, issued May 23, 2017, the disclosure of which is incorporated by reference.

The patient management program 123, or other trusted application, also maintains and safeguards the secure database 124 to limit access to patient EMRs 134 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 124. The physician would execute an application program 130 ("Pgm"), such as a post-monitoring ECG analysis program, on a personal computer 129 or other connectable computing device, and, through the application 130, coordinate access to his patient's EMRs 134 with the patient management program 123. Other schemes and safeguards to protect and maintain the integrity of patient EMRs 134 are possible.

Figure 4:
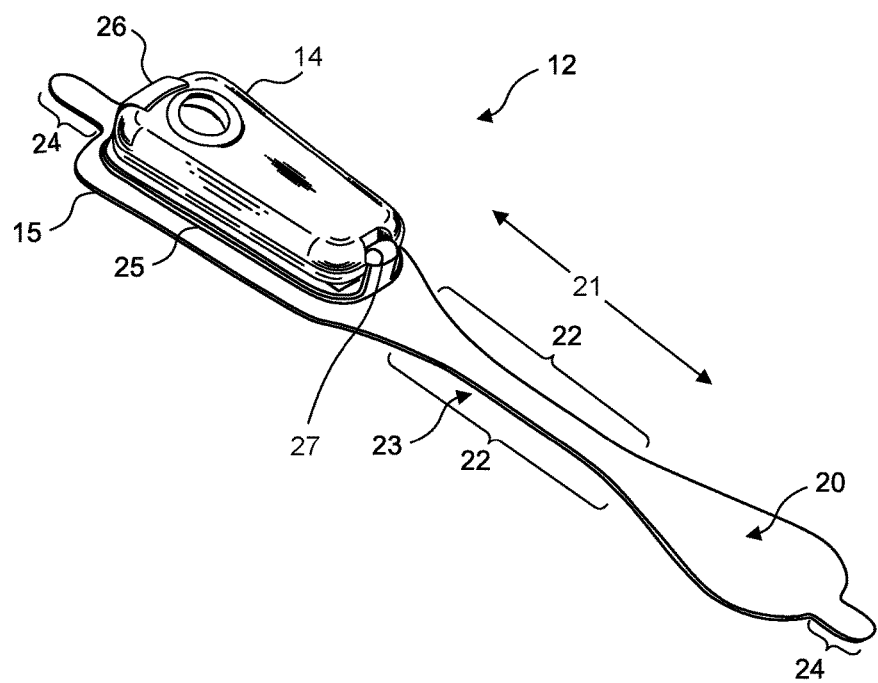
FIG. 4 is a perspective view showing an extended wear electrode patch with the combined monitor recorder in accordance with one embodiment.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 4 is a perspective view showing an extended wear electrode patch 15 with a monitor recorder 14 in accordance with one embodiment inserted. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above.

The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Pat. No. 9,545,204, issued Jan. 17, 2017, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, as further described infra beginning with reference to FIG. 9, as well as described in commonly-assigned U.S. Pat. No. 9,730,593, issued Aug. 15, 2017, the disclosure which is incorporated by reference. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
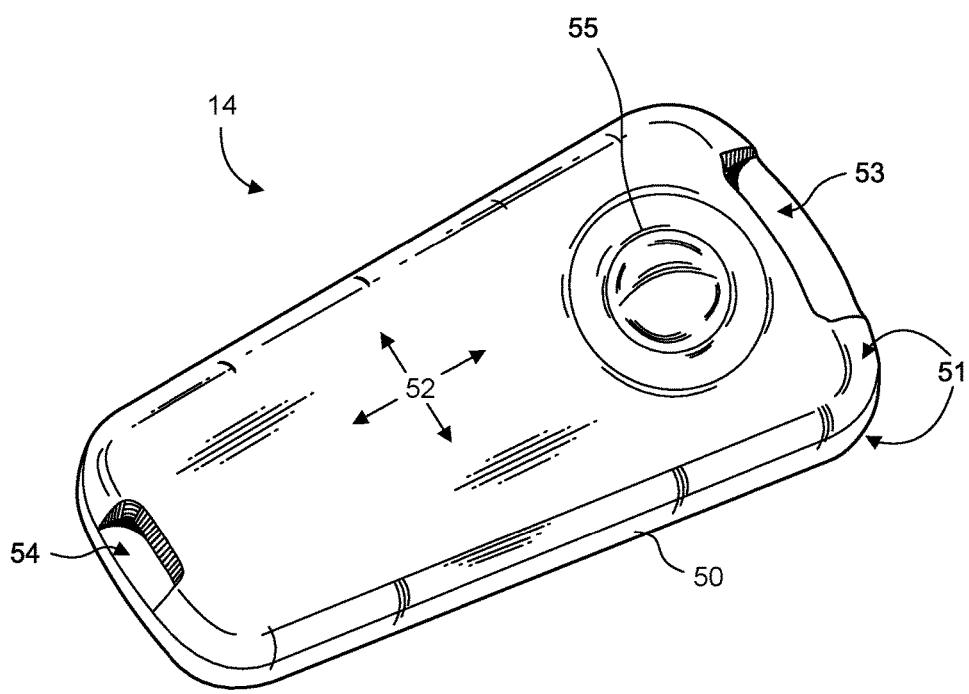
FIG. 5 is a perspective view showing the combined monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Pat. No. D717,955, issued Nov.

18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately on either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
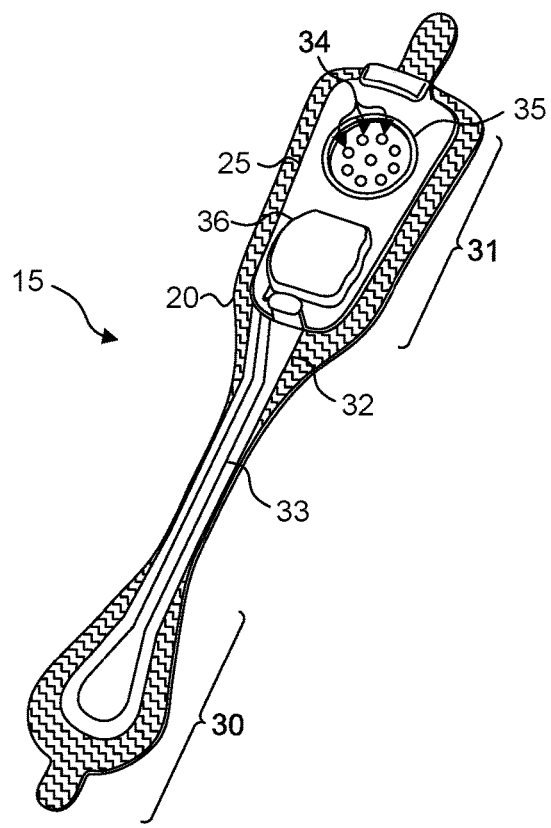
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 7:
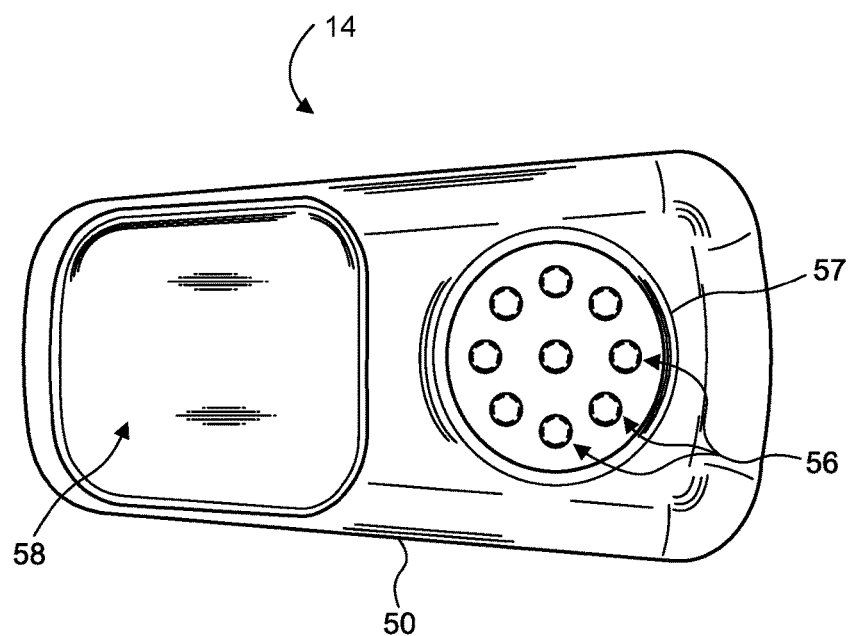
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 8:
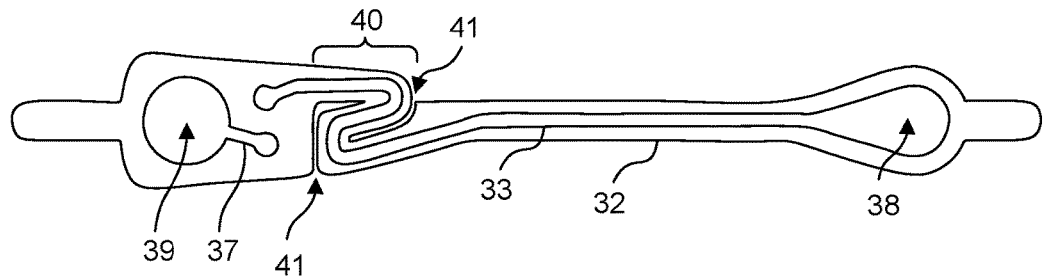
FIG. 8 is a top view showing the flexible circuit of the extended wear electrode patch of FIG. 3 when mounted above the flexible backing.

Unlike the flexible backing 20, the flexible circuit 32 is only able to bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 9:
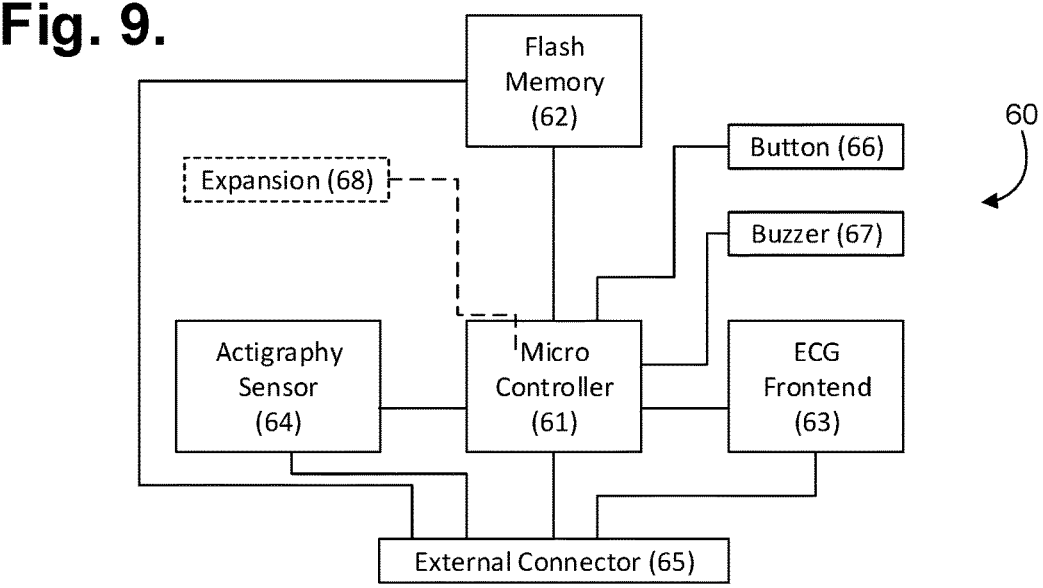
FIG. 9 is a functional block diagram showing the component architecture of the circuitry of the monitor recorder of FIG. 4.

ECG monitoring and other functions performed by the monitor recorder 14 are provided through a micro controlled architecture. FIG. 9 is a functional block diagram showing the component architecture of the circuitry 60 of the monitor recorder 14 of FIG. 4. The circuitry 60 is externally powered through a battery provided in the non-conductive receptacle 25 (shown in FIG. 6). Both power and raw ECG signals, which originate in the pair of ECG electrodes 38, 39 (shown in FIG. 8) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions.

Operation of the circuitry 60 of the monitor recorder 14 is managed by a microcontroller 61. The micro-controller 61 includes a program memory unit containing internal flash memory that is readable and writeable. The internal flash memory can also be programmed externally. The microcontroller 61 draws power externally from the battery provided on the electrode patch 15 via a pair of the electrical contacts 56. The microcontroller 61 connects to the ECG front end circuit 63 that measures raw cutaneous electrical signals and generates an analog ECG signal representative of the electrical activity of the patient's heart over time.

The circuitry 60 of the monitor recorder 14 also includes a flash memory 62, which the micro-controller 61 uses for storing ECG monitoring data and other physiology information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. During ECG monitoring, actigraphy becomes a recordable actigraphy event occurrence when the movement of the wearable monitor 12 and, therefore, the patient, exceeds a certain criteria threshold of acceleration or deceleration as detected by the actigraphy sensor 64, as further described infra with reference to FIG. 11. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses.

The microcontroller 61 includes an expansion port that also utilizes the communications bus. External devices, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the micro-controller 61 provided over one of the electrical contacts 56. The physiology sensor can include an SpO$_2$ sensor, blood pressure sensor, temperature sensor, respiratory rate sensor, glucose sensor, airflow sensor, volumetric pressure sensing, or other types of sensor or telemetric input sources. For instance, the integration of an airflow sensor is described in commonly-assigned U.S. Pat. No. 9,364,155, issued Jun. 14, 2016, the disclosure which is incorporated by reference. In a further embodiment, a wireless interface for interfacing with other wearable (or implantable) physiology monitors, as well as data offload and programming, can be provided as part of the circuitry 60 of the monitor recorder 14, or can be provided on the electrode patch 15 with communication with the microcontroller 61 provided over one of the electrical contacts 56, such as described in commonly-assigned U.S. Pat. No. 9,433,367, issued Sep. 6 2016, the disclosure of which is incorporated by reference.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible, such as described in commonly-assigned U.S. Pat. No. 9,730,593, Aug. 15, 2017, the disclosure which is incorporated by reference.

Figure 10:
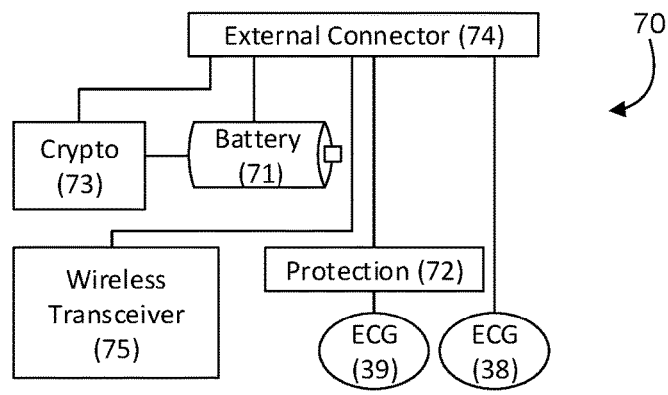
FIG. 10 is a functional block diagram showing the circuitry of the extended wear electrode patch of FIG. 4.

While the monitor recorder 14 operates under micro control, most of the electrical components of the electrode patch 15 operate passively. FIG. 10 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Finally, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 60.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14, such as described in commonly-assigned U.S. Pat. No. 9,655,538, issued May 23, 2017, the disclosure which is incorporated by reference.

Figure 11:
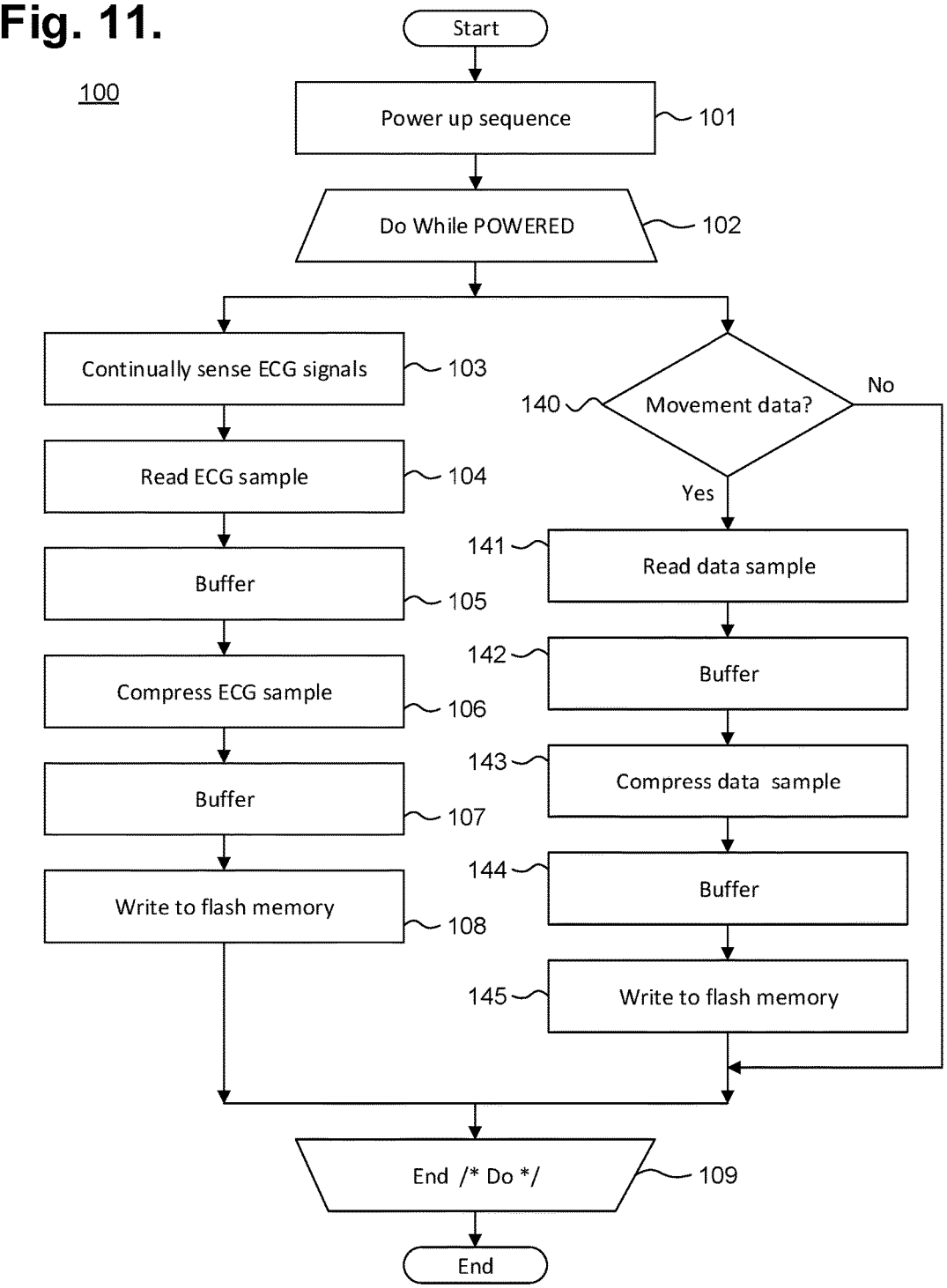
FIG. 11 is a flow diagram showing a monitor recorder-implemented method for monitoring ECG data and actigraphy data for use in the monitor recorder of FIG. 4.

The monitor recorder 14 continuously monitors the patient's heart rate and physiology. FIG. 11 is a flow diagram showing a monitor recorder-implemented method 100 for monitoring ECG data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 12:
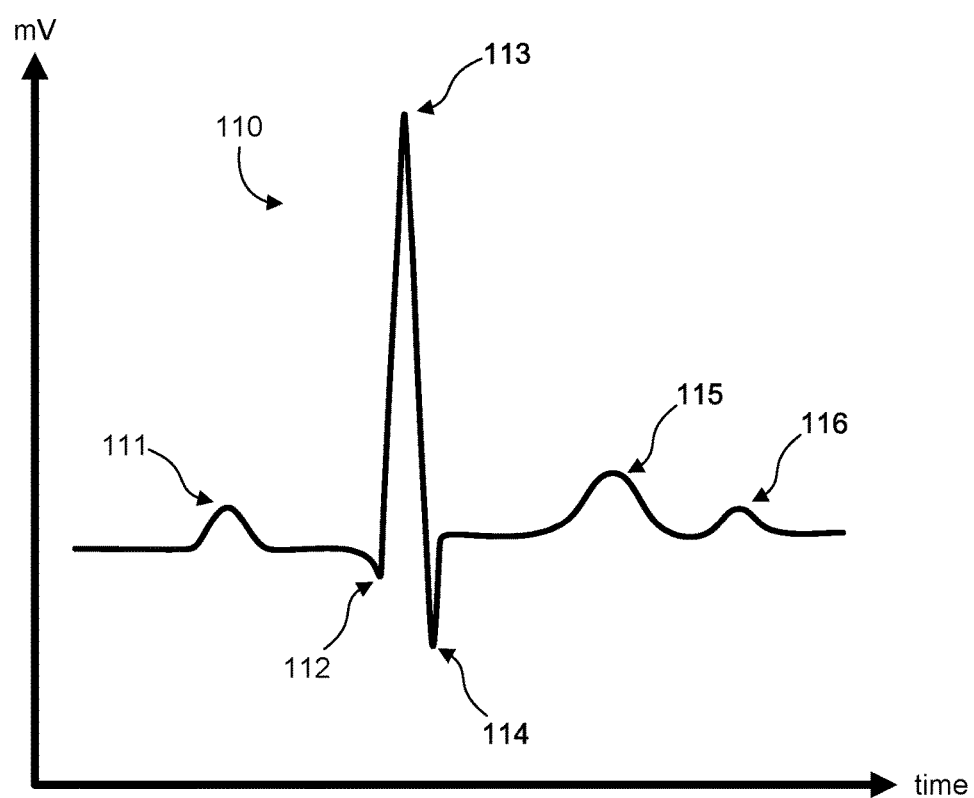
FIG. 12 is a graph showing, by way of example, a typical ECG waveform.

Following satisfactory completion of the power up sequence, an iterative processing loop (steps 102-109) is continually executed by the microcontroller 61. During each iteration (step 102) of the processing loop, the ECG frontend 63 (shown in FIG. 9) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal output front end 63. FIG. 12 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q-wave 112, followed by a larger upward deflection of an R-wave 113, and terminated with a downward waveform of the S-wave 114, collectively representative of ventricular depolarization. The T-wave 115 is normally a modest upward waveform, representative of ventricular depolarization, while the U-wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the extended wear ambulatory electrocardiography and physiological sensor monitor described herein is medically unique and important. The long-term observation of these ECG indicia, as provided through extended wear of the wearable monitor 12, provides valuable insights to the patient's cardiac function and overall well-being.

Each sampled ECG signal, in quantized and digitized form, is temporarily staged in buffer (step 105), pending compression preparatory to storage in the flash memory 62 (step 106). Following compression, the compressed ECG digitized sample is again buffered (step 107), then written to the flash memory 62 (step 108) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

The monitor recorder 14 also receives data from the actigraphy sensor 64. The data is received in a conceptually-separate execution thread as part of the iterative processing loop (step 102-109) continually executed by the microcontroller 61. During each iteration (step 102) of the processing loop, the actigraphy sensor 64 monitors a patient's movement and detects if there is a notable movement event, such as an event that may trigger or reflect a cardiovascular episode, that needs to be recorded as part of the monitoring (step 140). One example of a notable movement is a fall. When a patient sits still in a chair, an accelerometer records a g-force (g) equivalent to 1 g along the axis perpendicular towards the earth. If the patient falls from the chair, the accelerometer records a g-force equivalent to zero, or very close to zero, along the axis perpendicular towards the earth, during the freefall. Another example of a notable movement is a sudden acceleration or deceleration that is indicative of a forceful, traumatic impact on a patient, in which the g-force along at least one axis exceeds a certain threshold, for example, 2.5 g. Still another example is a series of accelerations and decelerations exceeding a certain threshold of g-force, indicating intensive physical exertions that may put undue stresses to heart. Other examples are possible. If no such notable movement events are detected, the method 100 proceeds to step 109. If a notable movement event is detected, the actigraphy sensor 64 provides an interrupt signal to the microprocessor 61, and the microprocessor 61 reads the data sample that includes the movement event and converts into a digital signal by the onboard ADC of the microcontroller 61 (step 141). This design provides an automatic time-correlation between a movement event and its corresponding ECG data. No additional software is needed to synchronize the accelerometer data and ECG data, resulting an efficient monitor recorder 14 and simplified post-recording processing.

During each iteration (step 102) of the processing loop, if movement data is detected (step 140), a sample of the movement telemetry is read (step 141) by the microcontroller 61 and, if necessary, converted into a digital signal by the onboard ADC of the microcontroller 61. Each sampled movement event, in quantized and digitized form, is temporarily staged in buffer (step 142), tending compression preparatory to storage in the flash memory subsystem 62 (step 143). Following compression, the compressed digitized movement sample is again buffered (step 144), then written to the flash memory subsystem 62 (step 145) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

The monitor recorder 14 stores ECG data and other information in the flash memory subsystem 62 (shown in FIG. 9) using a proprietary format that includes data compression. As a result, data retrieved from a monitor recorder 14 must first be converted into a format suitable for use by third party post-monitoring analysis software. FIG. 13 is a flow diagram showing a method 150 for offloading and converting ECG and other physiological data from an extended wear electrocardiography and physiological sensor monitor 12 in accordance with one embodiment. The method 150 can be implemented in software and execution of the software can be performed on a download station 125, which could be a programmer or other device, or a computer system, including a server 122 or personal computer 129, such as further described supra with reference to FIG. 3, as a series of process or method modules or steps. For convenience, the method 150 will be described in the context of being performed by a personal computer 136 or other connectable computing device (shown in FIG. 3) as middleware that converts ECG data and other information into a format suitable for use by a third-party post-monitoring analysis program. Execution of the method 150 by other computer system or download station 125 would be analogous mutatis mutandis.

Initially, the download station 125 is connected to the monitor recorder 14 (step 151), such as by physically interfacing to a set of terminals 128 on a paired receptacle 127 or by wireless connection, if available. The data stored on the monitor recorder 14, including ECG and physiological monitoring data, other recorded data, and other information are retrieved (step 152) over a hard link 135 using a control program 137 ("Ctl") or analogous application executing on a personal computer 136 or other connectable computing device.

The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 153-159) in an iterative processing loop. During each iteration (step 153), the ECG datum is read (step 154) and, if necessary, the gain of the ECG signal is adjusted (step 155) to compensate, for instance, for relocation or replacement of the electrode patch 15 during the monitoring period.

In addition, depending upon the configuration of the wearable monitor 12, other physiological data (or other information), including patient events, such as a fall, peak activity level, sleep detection, detection of patient activity levels and states, and so on, may be recorded along with the ECG monitoring data. For instance, actigraphy data may have been sampled by the actigraphy sensor 64 based on a sensed event occurrence, such as a sudden change in orientation due to the patient taking a fall. In response, the monitor recorder 14 will embed the actigraphy data samples into the stream of data, including ECG monitoring data, that is recorded to the flash memory 62 by the micro-controller 61. Post-monitoring, the actigraphy data is temporally matched to the ECG data to provide the proper physiological context to the sensed event occurrence. As a result, the three-axis actigraphy signal is turned into an actionable event occurrence that is provided, through conversion by the middleware, to third party post-monitoring analysis programs, along with the ECG recordings contemporaneous to the event occurrence. Other types of processing of the other physiological data (or other information) are possible.

In a further embodiment, other physiological data recorded is also read (step 156) and is time-correlated to the ECG monitoring data. For instance, blood pressure recorded by a blood pressure sensor would be temporally matched to the monitoring ECG data to provide the proper physiological context to the sensed event occurrence. Other types of processing of the other physiological data are possible.

Thus, during execution of the middleware, any other physiological data (or other information) that has been embedded into the recorded ECG monitoring data is read (step 156) and time-correlated to the time frame of the ECG signals that occurred at the time that the other physiological data (or other information) was noted (step 157). Finally, the ECG datum, signal gain adjusted, if appropriate, and other physiological data, if applicable and as time-correlated, are stored in a format suitable to the backend software (step 158) used in post-monitoring analysis.

In a further embodiment, the other physiological data, if apropos, is embedded within an unused ECG track. For example, the SCP-ECG standard allows multiple ECG channels to be recorded into a single ECG record. The monitor recorder 14, though, only senses one ECG channel. The other physiological data can be stored into an additional ECG channel, which would otherwise be zero-padded or altogether omitted. One example of the other physiological data is actigraphy data. The backend software would then be able to read the other physiological data in context with the single channel of ECG monitoring data recorded by the monitor recorder 14, provided the backend software implemented changes necessary to interpret the other physiological data. Still other forms of embedding of the other physiological data with formatted ECG monitoring data, or of providing the other physiological data in a separate manner, are possible.

Processing continues (step 159) for each remaining ECG datum, after which the processing loop is exited and execution terminates. Still other operations and steps are possible.

Figure 14:
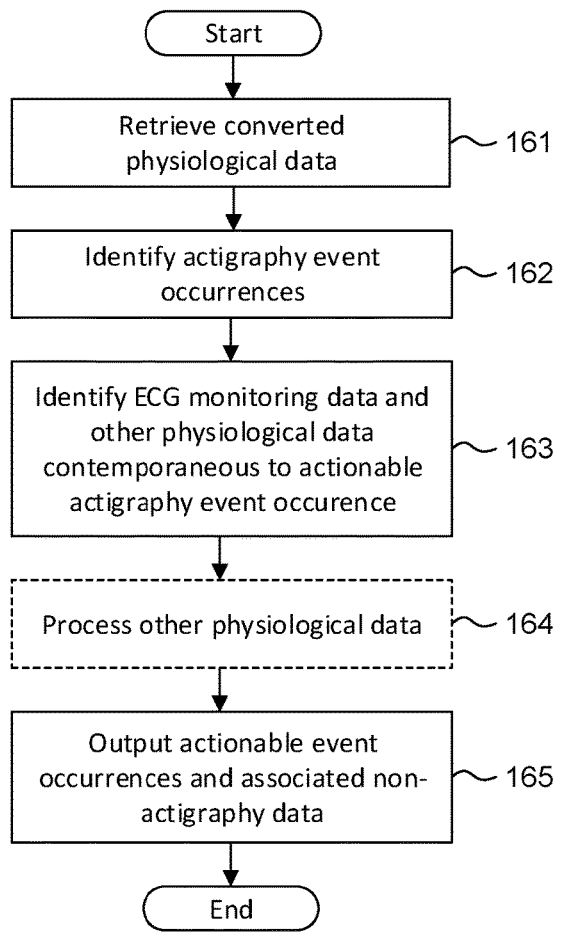
FIG. 14 is a method 160 for processing data collected by the combined ECG and actigraphy monitor in accordance with one embodiment.

The occurrence of actigraphy events are monitored by the monitor recorder 14 through the actigraphy sensor 64 of the circuitry 60 (shown in FIG. 9). The data collected by the monitor recorder 14 can be further processed by the application software to correlate the actigraphy event occurrences with ECG and other non-movement physiological data, if applicable. FIG. 14 is a flow diagram showing a method 160 for processing actigraphy data collected by a monitor recorder 14 in accordance with one embodiment. Physiological data includes actigraphy data, ECG monitoring data and, if applicable, other physiological data. Physiological data is offloaded and converted as described supra with reference to FIG. 13. The converted physiological data is then retrieved by the backend software (step 161). The backend software processes the retrieved physiological data to identify recorded actigraphy event occurrences (step 162).

During ECG monitoring, actigraphy becomes a recordable actigraphy event occurrence when the movement of the wearable monitor 12 and, therefore, the patient, exceeds a certain criteria threshold of acceleration or deceleration as detected by the actigraphy sensor 64. Ordinarily, movement of a patient is continual, but, for the most part, not rising to the level of an event occurrence. For instance, the rise and fall of a patient's chest attendant to regular breathing constitutes movement, yet such movement is ordinary and expected. Recording each occurrence of ordinary and expected movement of this sort is not necessary, and the actigraphy sensor 64 would be set per a stored criteria to ignore those movement failing to warrant recordation (as event occurrences) through onboard parameters that specify the conditions under which actigraphy will be recorded as event occurrences, such as described supra with reference to FIG. 11. For instance, the onboard parameters could be set to trigger actigraphy recordation when the g-force along at least one axis exceeds a certain criteria threshold, for example, 2.5 g, although other thresholds could be used. However, when a patient appears to have fallen, the movement of the patient will be both sudden and relatively dramatic in comparison to, say, regular breathing. Such movement will be recorded as an actigraphy event occurrence.

In addition, certain actigraphy event occurrences are considered to be actionable, that is, of sufficient importance to warrant flagging for further consideration to a following physician. For instance, the occurrence of a fall event could signal the onset of myocardial infarction in the patient, or, under different circumstances, could be found to have been precipitated by myocardial infarctional onset. The occurrence of an actigraphy event is identified as actionable based on a filtering criteria. Actionable actigraphy event occurrences include, for instance, sleep, awake, hyperactivity, and falling, although other actionable actigraphy event occurrences are possible. Both the occurrence of the actigraphy event, that is, the fall, and the patient's ECG monitoring data, as well as any other available physiological data, may be of diagnostic interest and are identified (step 163). In turn, a physician would scrutinize the identified physiological data, including the ECG monitoring data and the actigraphy event occurrence, for accompanying indications of myocardial infarction, or other concerns relating to syncope and related maladies.

Other types of physiological data may include data recorded by other physiology sensors including the $SpO_2$ sensor, blood pressure sensor, temperature sensor, glucose sensor, airflow sensor, volumetric pressure sensing, or other types of sensor or telemetric input sources. In this example, is a blood pressure sensor were available to record blood pressure substantially concurrent to the monitoring of ECG and actigraphy, the retrieved blood pressure data would be temporally aligned with the physiological data relating to the patient's fall and thereby help to diagnostic efficacy. Optionally, these other physiological data may be processed according to diagnostic and prognostic values of the data (step 164). Finally, the information about the actigraphy events, such as the time the events occurred, the duration of the events, the nature of the event (intensity of the fall, for example), together with the other approximately physiological data relevant for diagnosis, are output for consultation by a physician or another medical professional (step 165). Still other operations and steps are possible. Other types of processing the other physiological data are possible.

While the invention has been particularly shown and described as referenced to the embodiments thereof, those skilled in the art will understand that the foregoing and other changes in form and detail may be made therein without departing from the spirit and scope.

What is claimed is:
1. An electrocardiography and actigraphy monitoring system, comprising:
 a monitor recorder, comprising:
  a sealed housing adapted to be removably secured into a non-conductive receptacle on a disposable extended wear electrode patch;
  electronic circuitry comprised within the sealed housing, comprising:
   an externally-powered flash memory electrically interfaced with an externally-powered micro-controller and comprising a data record comprising at least two electrocardiogram (ECG) tracks, each of the ECG tracks operable to store ECG data from an ECG data channel;
   an electrocardiographic front end circuit electrically interfaced to the externally-powered micro-controller and operable to sense electrocardiographic signals through electrocardiographic electrodes provided on the disposable extended wear electrode patch;
   an actigraphy sensor electrically interfaced with the micro-controller and operable to sense one or more actigraphy event occurrences based on movement of the sensor using an actigraphy event occurrence criteria and to send an interrupt request (IRQ) signal to the micro-controller upon sensing each of the actigraphy event occurrences; and
   an externally-powered micro-controller operable to execute under micro-programmable control, the micro-controller further operable to sample the electrocardiographic signals and to sample one of the actigraphy event occurrences sensed by the actigraphy sensor upon receiving one of the IRQ signals, to embed samples of the electrocardiographic signals within one of the ECG tracks for storage into the data record in the memory and to embed the samples of the actigraphy event occurrences into another one of the ECG tracks for storage into the data record in the memory, the embedding of the samples of the actigraphy event occurences comprising buffering each of the actigraphy event occurrences samples, compressing each of the buffered actigraphy event occurrences samples, buffering each of the compressed actigraphy event occurrences samples, and writing the buffered compressed actigraphy event occurrences samples into the another one of ECG tracks.

2. A system according to claim 1, wherein the format of the data record is Standard communications.

3. A system according to claim 1, further comprising:
 the disposable extended wear electrode patch comprising:
 a flexible backing formed of an elongated strip of stretchable material with a narrow longitudinal midsection and, on each end, a contact surface at least partially coated with an adhesive dressing provided as a crimp relief;
 the pair of electrocardiographic electrodes conductively exposed on the contact surface of each end of the elongated strip, respectively;
 the receptacle adhered to an outward-facing surface of the elongated strip and comprising a plurality of electrical pads; and
 a flexible circuit affixed on each end of the elongated strip as a strain relief and comprising a pair of circuit traces electrically coupled to the pair of electrocardiographic electrodes and a pair of the electrical pads.

4. A system according to claim 3, further comprising:
 a battery comprised on the disposable extended wear electrode patch and electrically interfaced to a pair of the electrical pads; and at least one of:
 the micro-controller operable to draw power from the battery via the pair of the electrical pads; and the flash memory operable to draw power from the battery via the pair of the electrical pads.

5. A system according to claim 4, further comprising:
an expansion bus operatively interconnected to the micro-controller and electrically coupled to at least one of the electrical pads;
a physiology sensor comprised within the disposable extended wear electrode patch and operable to sense physiology and to draw power from the battery, the physiology sensor electrically interfaced with the micro-controller over the expansion bus; and
the flash memory further operable through the expansion bus to store samples of the physiology sensed by the physiology sensor.

6. A system according to claim 5, wherein the physiology sensor is selected from the group comprising an $SpO_2$ sensor, a blood pressure sensor, a temperature sensor, a respiratory rate sensor, a glucose sensor, an air flow sensor, and a volumetric pressure sensor.

7. A system according to claim 4, further comprising:
an expansion bus operatively interconnected to the micro-controller;
a physiology sensor comprised within the reusable electrocardiography monitor and operable to sense physiology and to draw power from the battery via the pair of the electrical pads, the physiology sensor electrically interfaced with the micro-controller over the expansion bus; and
the flash memory further operable through the expansion bus to store samples of the physiology sensed detected by the physiology sensor.

8. A system according to claim 7, wherein the physiology sensor is selected from the group comprising an $SpO_2$ sensor, a blood pressure sensor, a temperature sensor, a respiratory rate sensor, a glucose sensor, an air flow sensor, and a volumetric pressure sensor.

9. A system according to claim 1, further comprising:
a server computer system centrally accessible over a data communications network and comprising a processor configured to execute program code stored in a memory, comprising:
    a data retrieval module configured to retrieve the samples of the electrocardiographic signals and the samples of the actigraphy event occurrences from the flash memory of the electronic circuitry;
    an evaluation module configured to identify an actionable actigraphy event occurrence from the samples of the actigraphy event occurrences based on a filtering criteria;
    a correlation module configured to identify those samples of the electrocardiographic signals that were sensed substantially concurrent to a time of the occurrence of the actionable actigraphy event; and
    an output module configured to output the actionable event occurrence and the samples of the electrocardiographic signals that were identified.

10. A system according to claim 9, wherein the filtering criteria is selected from the group comprising sleep, awake, hyperactivity, and falling.

11. A system according to claim 9, further comprising:
a patient management program executed by the server computer system configured to store the samples of the electrocardiographic signals and the samples of the actigraphy event occurrences into a secure database using a data communications network; and
the secure database interconnected to the data communications network and operable to maintain the samples of the electrocardiographic signals on behalf of the server computer system.

12. A system, according to claim 11, further comprising:
a subscription module configured to implemented a subscription service that controls authorization of a duration of an operation of the monitor recorder and parameters of the operation.

13. A system according to claim 1, further comprising
a download station comprising:
    a non-conductive receptacle adapted to removably receive the monitor recorder; and
    a download station controller operable to retrieve the samples of the electrocardiographic signals and the samples of the actigraphy event occurrences from the flash memory; and
a computer system operatively coupled to the download station controller and centrally accessible over a data communications network and operable to maintain the samples of the electrocardiographic signals and the samples of the actigraphy event occurrences upon retrieval.

14. A system to claim 1, further comprising
a download station configured to wirelessly interface with the monitor recorder and to wirelessly retrieve the samples of the electrocardiographic signals and the samples of the actigraphy event occurrences from the flash memory.

15. A system according to claim 1, further comprising:
an analog-to-digital converter comprised within the micro-controller and configured to digitize the samples of the actigraphy event occurrences.

16. A system to claim 1, further comprising:
a three-axis accelerometer comprised in the actigraphy sensor, the actigraphy event occurrence criteria comprising a threshold of acceleration or deceleration along at least one of the axes of the three-axis accelerometer.

17. An extended wear electrocardiography and physiological sensor monitor according to claim 1, wherein the electrocardiographic front end circuit is optimized to sense P-wave signals in the electrocardiographic signals.

18. A system according to claim 1, wherein the actigraphy event occurrence criteria comprise at least one of a threshold of acceleration or deceleration of the sealed housing.

19. A system according to claim 18, wherein acceleration or deceleration of the sealed housing is expressed based on recorded g– the threshold force.

* * * * *